United States Patent
Abraham et al.

(10) Patent No.: US 11,834,403 B2
(45) Date of Patent: *Dec. 5, 2023

(54) RECOVERY OF 3-HYDROXYPROPIONIC ACID

(71) Applicant: CARGILL, INCORPORATED, Wayzata, MN (US)

(72) Inventors: Timothy Walter Abraham, Minnetonka, MN (US); Erik Allen, Minneapolis, MN (US); John J. Hahn, Apple Valley, MN (US); Paraskevas Tsobanakis, Mendota Heights, MN (US); Eric Christopher Bohnert, Minneapolis, MN (US); Christopher Lawrence Frank, Maple Grove, MN (US)

(73) Assignee: CARGILL, INCORPORATED, Wayzata, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/649,398

(22) Filed: Jan. 31, 2022

(65) Prior Publication Data

US 2022/0153677 A1    May 19, 2022

Related U.S. Application Data

(63) Continuation of application No. 16/601,069, filed on Oct. 14, 2019, now Pat. No. 11,236,037, which is a
(Continued)

(51) Int. Cl.
*C07C 51/44* (2006.01)
*B01D 3/00* (2006.01)
(Continued)

(52) U.S. Cl.
CPC .............. *C07C 51/44* (2013.01); *B01D 3/002* (2013.01); *B01D 3/10* (2013.01); *B01D 3/34* (2013.01);
(Continued)

(58) Field of Classification Search
CPC ....... C07C 51/44; C07C 51/412; C07C 51/42; C07C 59/01; B01D 3/002; B01D 3/10; B01D 3/34; B01D 15/363; C12P 7/42
See application file for complete search history.

(56) References Cited

U.S. PATENT DOCUMENTS

| 4,855,494 A | * | 8/1989 | Margureanu | ........... C12M 21/12 562/580 |
| 5,274,073 A | | 12/1993 | Gruber | |

(Continued)

FOREIGN PATENT DOCUMENTS

| AT | 508663 A4 | * | 3/2011 | ................ C12P 7/42 |
| AT | 5086634 A | | 3/2011 | |

(Continued)

OTHER PUBLICATIONS

AT508663A4_ENG (Espacenet machine translation of Edlauer) (Year: 2011).*

(Continued)

*Primary Examiner* — Gabriel E Gitman

(57) ABSTRACT

A method for recovering a composition enriched in 3-hydroxypropionic acid by providing the fermentation broth, acidifying the fermentation broth; reducing the total sulfate ion and phosphate ion concentration of the resulting aqueous solution to produce a reduced ion aqueous solution; distilling the resulting reduced ion aqueous solution and recovering the resulting aqueous distillation product comprising 3-hydroxypropionic acid.

5 Claims, 4 Drawing Sheets

Related U.S. Application Data continuation of application No. 14/777,009, filed as application No. PCT/US2014/028793 on Mar. 14, 2014, now Pat. No. 10,442,749.

(60) Provisional application No. 61/793,687, filed on Mar. 15, 2013.

(51) Int. Cl.

| | | |
|---|---|---|
| *B01D 3/10* | (2006.01) | |
| *C07C 51/42* | (2006.01) | |
| *C12P 7/42* | (2006.01) | |
| *C07C 51/41* | (2006.01) | |
| *B01D 3/34* | (2006.01) | |
| *B01D 15/36* | (2006.01) | |

(52) U.S. Cl.
 CPC .......... *B01D 15/363* (2013.01); *C07C 51/412* (2013.01); *C07C 51/42* (2013.01); *C12P 7/42* (2013.01)

(56) References Cited

U.S. PATENT DOCUMENTS

| | | | |
|---|---|---|---|
| 6,489,508 B1 | 12/2002 | Van Gansbeghe | |
| 7,326,557 B2 | 2/2008 | San | |
| 7,560,579 B2 | 7/2009 | Te Baay | |
| 7,846,688 B2 | 12/2010 | Gill | |
| 7,987,056 B2 | 7/2011 | Gill | |
| 8,048,624 B1 | 11/2011 | Lynch | |
| 8,337,663 B2 | 12/2012 | Xu | |
| 8,467,975 B2 | 6/2013 | Ryan | |
| 8,652,816 B2 | 2/2014 | Lynch | |
| 8,809,027 B1 | 8/2014 | Lynch | |
| 10,442,748 B2 * | 10/2019 | Abraham | B01D 3/002 |
| 10,442,749 B2 * | 10/2019 | Abraham | B01D 3/002 |
| 11,236,036 B2 * | 2/2022 | Abraham | B01D 15/363 |
| 11,236,037 B2 * | 2/2022 | Abraham | C07C 51/412 |
| 2004/0210087 A1 | 10/2004 | Meng | |
| 2005/0221457 A1 | 10/2005 | Tsobanakis | |
| 2005/0272135 A1 | 12/2005 | Datta | |
| 2007/0015936 A1 | 1/2007 | Meng | |
| 2008/0119626 A1 | 5/2008 | Fujimaru | |
| 2009/0325248 A1 | 12/2009 | Marx | |
| 2010/0099910 A1 | 4/2010 | Meng | |
| 2011/0089016 A1 | 4/2011 | Winkelaar | |
| 2011/0105791 A1 | 5/2011 | Kuppinger | |
| 2011/0125118 A1 | 5/2011 | Lynch | |
| 2012/0010372 A1 | 1/2012 | Fujino | |
| 2012/0160686 A1 | 6/2012 | Jump | |
| 2013/0281649 A1 * | 10/2013 | Yoshida | C07C 51/377 562/599 |
| 2014/0121118 A1 | 5/2014 | Warner | |
| 2015/0057455 A1 | 2/2015 | Hoppe | |

FOREIGN PATENT DOCUMENTS

| | | | | |
|---|---|---|---|---|
| EP | 2660235 A1 | | 11/2013 | |
| JP | 2010126512 A | * | 6/2010 | ............. C07C 51/43 |
| JP | 2013023481 A | * | 2/2013 | ........... C07C 51/377 |
| JP | 2013023481 A | | 2/2013 | |
| JP | 2013505727 A | | 2/2013 | |
| JP | 2012091114 A1 | | 6/2014 | |
| WO | 0242418 W | | 5/2002 | |
| WO | 03062173 W | | 7/2003 | |
| WO | 2003082795 A2 | | 10/2003 | |
| WO | 2004041421 A2 | | 5/2004 | |
| WO | 2005003074 A1 | | 1/2005 | |
| WO | 2005118719 A2 | | 12/2005 | |
| WO | 2007130745 A1 | | 11/2007 | |
| WO | 2008021765 A2 | | 2/2008 | |
| WO | 2008027742 A1 | | 3/2008 | |
| WO | 2008089102 A2 | | 7/2008 | |
| WO | 2010006076 A2 | | 1/2010 | |
| WO | 2010011874 A2 | | 1/2010 | |
| WO | 2010017230 A2 | | 2/2010 | |
| WO | 2010031083 A2 | | 3/2010 | |
| WO | 2011038364 A1 | | 3/2011 | |
| WO | 2011063363 A2 | | 5/2011 | |
| WO | 2011094457 A1 | | 8/2011 | |
| WO | 2012074818 A2 | | 6/2012 | |
| WO | 2013192450 A1 | | 12/2013 | |
| WO | 2013192451 A1 | | 12/2013 | |
| WO | 2013192453 A1 | | 12/2013 | |
| WO | 2014144367 A1 | | 9/2014 | |
| WO | 2014144400 A1 | | 9/2014 | |
| WO | 2014145096 A1 | | 9/2014 | |
| WO | 2014145297 A1 | | 9/2014 | |
| WO | 2014145332 A1 | | 9/2014 | |
| WO | 2014145334 A1 | | 9/2014 | |
| WO | 2014145343 A1 | | 9/2014 | |
| WO | 2014145344 A2 | | 9/2014 | |
| WO | 2014146026 A1 | | 9/2014 | |
| WO | 2014146047 A1 | | 9/2014 | |
| WO | 2015010103 A2 | | 1/2015 | |

OTHER PUBLICATIONS

JP2010126512A_ENG (Espacenet machine translation of Kawamura) (Year: 2010).*

JP2013023481A_ENG (Espacenet machine translation of Yoshida) (Year: 2013).*

Cie, et al., "Renewable Acrylic Acid", (Renewable Acrylic Acid. University of Pennsylvania Scholarly Commons, Apr. 2012, p. 58) (Year: 2012).

* cited by examiner

RECOVERY OF 3-HYDROXYPROPIONIC ACID

CROSS-REFERENCE TO RELATED APPLICATIONS

This application is a Continuation of U.S. patent application Ser. No. 16/601,069, filed Oct. 14, 2019, which is a Continuation of U.S. Pat. No. 10,442,749, issued Oct. 15, 2019, which is a national phase application of International Application No. PCT/US2014/028793, filed Mar. 14, 2014, which claims the benefit of U.S. Provisional Patent Application No. 61/793,687, filed Mar. 15, 2013, each of which is hereby incorporated by reference in its entirety.

FIELD OF THE INVENTION

The present invention relates to recovery of 3-hydroxypropionic acid thereof from a fermentation broth. More specifically, the present invention relates to recovery of 3-hydroxypropionic acid from a fermentation broth by processing steps.

BACKGROUND OF THE INVENTION

Hydroxycarboxylic acid monomers are useful in many applications, and can be prepared by a number of routes. One method of manufacture includes the use of fermentation, which can produce a number of fermentation products, depending on the fermenting organism selected and other factors. See, for example, U.S. Pat. No. 8,337,663.

SUMMARY OF THE INVENTION

3-Hydroxypropionic acid ("3HP") in particular is a desired material that is useful for many industrial applications. It has been discovered that efficient recovery of 3HP in concentrations and desired purity that is suitable for certain industrial applications is challenging. In particular, process steps intended to efficiently recover 3HP can lead to recovery solutions that either do not contain an appropriate concentration of 3HP for the use in a subsequent process, or can lead to introduction of undesired impurities. For example, it is challenging to recover 3HP in desired concentrations without dehydrating the 3HP to form acrylic acid in undesirable concentrations. This is particularly the case when recovering 3HP on a commercially viable scale. Separations and systems that are suitable for use on the lab bench may not be feasible for use at commercial production levels, and introduction of different techniques on scale-up introduce new challenges and unexpected results. The present invention provides an advantageous process for recovery of 3HP.

Specifically, a method is provided for recovering a composition enriched in 3-hydroxypropionic acid from a fermentation broth comprising 3-hydroxypropionic acid and/or salts thereof. The method comprises the steps of:
 (a) providing the fermentation broth having a pH of from about 2 to about 8 comprising:
  3-hydroxypropionic acid and/or salts thereof, and
  a total sulfate ion and phosphate ion concentration;
 (b) increasing the concentration of 3-hydroxypropionic acid and/or salts thereof in the fermentation broth of step (a) to from about 100 to about 500 grams of 3-hydroxypropionic acid equivalents per liter of broth by evaporating at least a portion of the liquid present in the fermentation broth
 (c) acidifying the fermentation broth to lower the pH to from about 1 to about 3 to form an aqueous solution comprising 3-hydroxypropionic acid;
 (d) reducing the total sulfate ion and phosphate ion concentration of the aqueous solution to produce a reduced ion aqueous solution comprising 3-hydroxypropionic acid;
 (e) distilling the reduced ion aqueous solution at a pH of from about 1 to about 3 by applying vacuum and heat to the reduced ion aqueous solution to form an aqueous distillation product comprising 3-hydroxypropionic acid; and
 (f) recovering the aqueous distillation product comprising 3-hydroxypropionic acid at a concentration of at least thirty percent by weight of the aqueous distillation product and wherein the distillation product comprises less than five parts by weight acrylic acid per one hundred parts by weight 3-hydroxypropionic acid present.

In some aspects, the fermentation broth comprises a total sulfate ion and phosphate ion concentration of at least 50 ppm, for example, a sulfate ion and phosphate ion concentration of at least 100 ppm, at least 200 ppm, or at least 400 ppm. In some aspects the fermentation broth comprises a sulfate ion and phosphate ion concentration of at least 4,000 ppm.

In some aspects the total sulfate ion and phosphate ion concentration of the reduced ion aqueous solution from step (d) is less than 15,000 ppm, for example: less than 10,000 ppm, less than 5,000 ppm, less than 3,000 ppm, less than 2,500 ppm, less than 2,000 ppm, less than 1,500 ppm total sulfate ion and phosphate ion concentration, and when particularly low ion levels are desirable, a total sulfate ion and phosphate ion concentration of less than 1,000 ppm.

BRIEF DESCRIPTION OF THE DRAWINGS

The accompanying drawings, which are incorporated in and constitute a part of this application, illustrate several aspects of the invention and together with a description of the embodiments serve to explain the principles of the invention. A brief description of the drawings is as follows.

DETAILED DESCRIPTION OF PRESENTLY PREFERRED EMBODIMENTS

Figure 1:
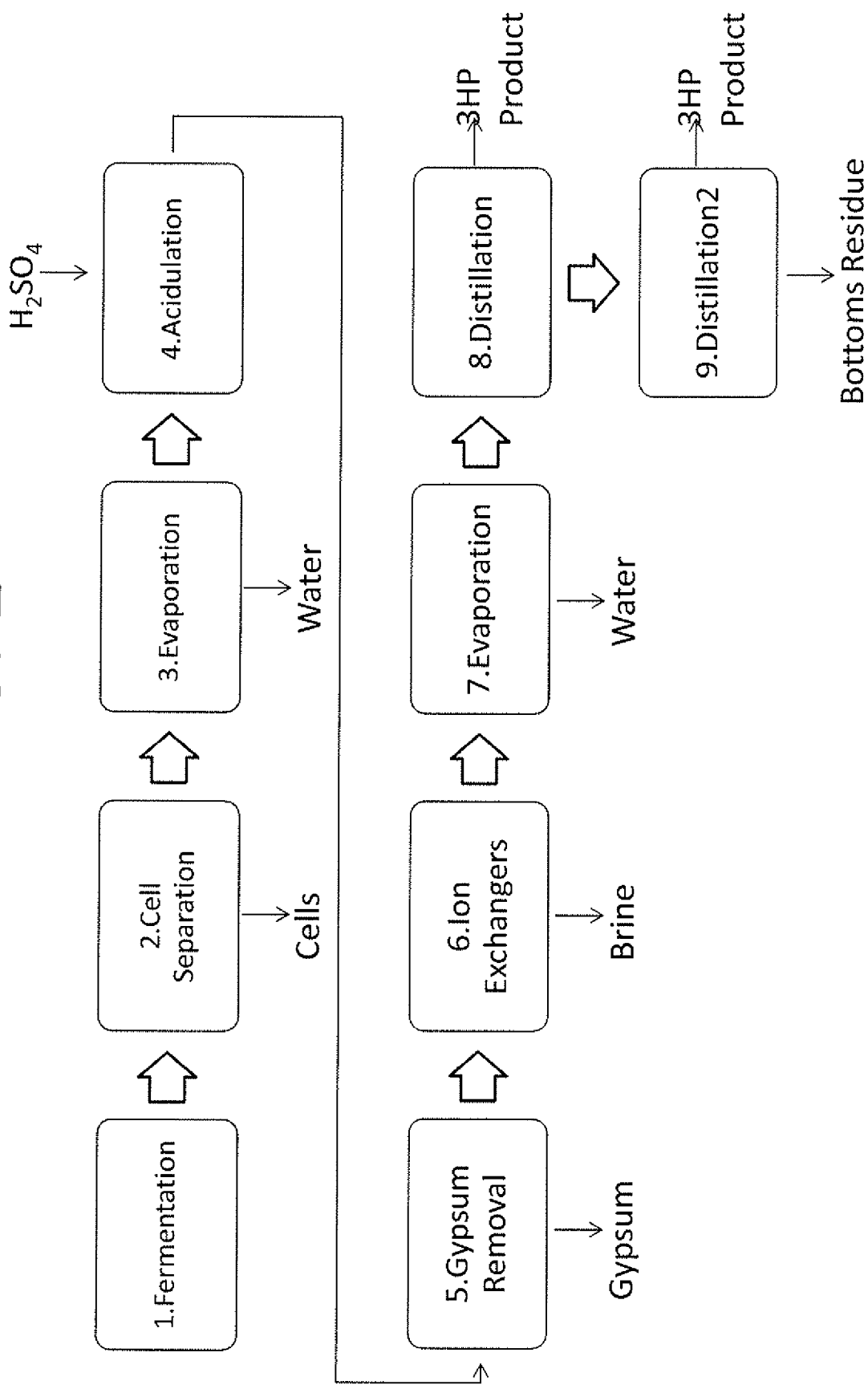
FIG. 1 is a process flow diagram of one embodiment of the present method.

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

3-Hydroxypropionic acid and/or salts thereof is generated by a fermentation process using known fermentation techniques. For purposes of the present discussion, 3-hydroxypropionic acid and/or salts (and similar statements such as "3HP (and salts thereof)", etc) means that the compound 3-hydroxypropionic acid is present either in its acid form or in a salt form or in a mixture of the acid form and the salt form. The salt form may comprise one or more counterions.

In step (a) of the present process, a fermentation broth is provided having a pH of from about 2 to about 8 comprising 3-hydroxypropionic acid and/or salts thereof, and a total sulfate ion and phosphate ion concentration of typically at least 50 ppm, for example at least about 100 ppm, at least about 200 ppm, at least 400 ppm, and in some instances at least about 4,000 ppm. In an embodiment, the fermentation broth has a pH of from about 2 to about 5 in step (a). In another embodiment, the fermentation broth has a pH of from about 2.5 to about 4.5 in step (a). Lower pH levels of the fermentation broth are advantageous for certain fermentation organisms that can ferment at commercially acceptable rates at low pH.

In an embodiment, the concentration of 3-hydroxypropionic acid and/or salts thereof in the fermentation broth of step (a) is from about 30 to about 200 grams of 3-hydroxypropionic acid equivalents per liter of broth. In another embodiment, the concentration of 3-hydroxypropionic acid and/or salts thereof in the fermentation broth of step (a) is from about 60 to about 150 grams of 3-hydroxypropionic acid equivalents per liter of broth. In another embodiment, the concentration of 3-hydroxypropionic acid and/or salts thereof in the fermentation broth of step (a) is from about 70 to about 130 grams of 3-hydroxypropionic acid equivalents per liter of broth.

In step (b) the concentration of 3-hydroxypropionic acid and/or salts thereof in the fermentation broth of step (a) is increased to from 100 to 500 grams of 3-hydroxypropionic acid equivalents per liter of broth by evaporating a portion of the liquid present in the fermentation broth at a broth temperature of from 60° C. to 100° C. In an embodiment, the concentration of 3-hydroxypropionic acid and/or salts thereof in the fermentation broth is increased to from 250 to 400 grams, and in some aspects from 140 to 400 grams, from 150 to 350 grams, from 200 to 330 grams, from 220 to 320 grams, or from 230 to 300 grams of 3-hydroxypropionic acid equivalents per liter of broth.

The increase of concentration of 3-hydroxypropionic acid in this step is particularly advantageous in providing both an economic process and also in reducing introduction of undesired side products or impurities. In an embodiment, the evaporation of liquid takes place at a broth temperature of from about 70° C. to about 90° C. In an embodiment, the evaporation of liquid takes place at a pressure of from about 250 to about 300 Torr.

In step (c) of the present process, the fermentation broth is acidified to lower the pH to from about 1 to about 3 to form an aqueous solution comprising 3-hydroxypropionic acid. It has been found that reducing the pH of the aqueous solution comprising 3-hydroxypropionic acid provides processing benefits when 3-hydroxypropionic acid is in the acid form, and is beneficial for the recovery of 3-hydroxypropionic acid. In an embodiment, the pH of the fermentation broth is lowered to a pH of from about 1.5 to about 2.5 in step (c), and in some aspects from a pH of 1.5 to a pH of 2.0.

During the fermentation process, various ingredients are added to the fermentation broth to establish and maintain favorable nutrition and pH conditions to support the particular organism carrying out the fermentation. After completion of the fermentation, various ionic species are present that are desirable to remove. The removal of certain ions is facilitated in the acidification step through the formation of insoluble and/or easily isolatable compounds. For example, undesired calcium present in the fermentation broth is removed by lowering the pH through the addition of $H_2SO_4$ or other acidic compounds that will form insoluble and/or easily isolatable compounds with calcium. Addition of $H_2SO_4$ is preferred because the resulting isolatable compound is gypsum. The insoluble and/or easily isolatable compounds are removed by conventional equipment, such as use of a centrifuge, a belt filter, a drum filter, or membrane filter, or other appropriate separation techniques.

In an embodiment of the present invention, cells from the fermentation process are preferably removed from the fermentation broth prior to addition of acid, so the amount of biological materials present in the gypsum or like material that is removed is below the amount suitable for end use of this product. Alternatively, the cells may be removed after the acidification step (c), together with the removal of insoluble and/or easily isolatable compounds that may be formed during the acidification step.

In step (d) of the present process, the total sulfate ion and phosphate ion concentration of the aqueous solution is reduced. Typically, the total sulfate ion and phosphate ion concentration of the reduced ion aqueous solution produced in step (d) is less than 15,000 ppm. Reduction of the ion content in the aqueous solution prior to distillation is advantageous, because it has been found that carrying out these steps in this order reduces the amount of undesired side products and impurities present in the final recovered distillation product. In particular, reduction of the ion content of the aqueous solution prior to distillation beneficially reduces the amount of acrylic acid formed in subsequent steps of the 3-hydroxypropionic acid recovery process, and also reduces the boiling point of the reduced ion aqueous solution, and reduces the energy needed to recovery the 3HP. In an embodiment, the total sulfate ion and phosphate ion concentration is reduced to less than about 10,000 ppm, less than about 5000 ppm, less than about 3000 ppm, less than 2,500 ppm, less than 2,000 ppm, less than 1,500 ppm, and when particularly low ion levels are desirable, a total sulfate ion and phosphate ion concentration of less than 1,000 ppm in step (d). In an embodiment, the step (d) of reducing the total sulfate ion and phosphate ion concentration of the aqueous solution is carried out by utilizing an ion exchanger. In an embodiment, the ion exchanger comprises an anion exchange resin. In an embodiment, the amount of positively charged ions in the aqueous solution is reduced by use of an ion exchanger that comprises a cation exchange resin. In an embodiment of the present invention, negative ion reduction has a tendency to increase the pH of the aqueous solution, which is preferably at least partially counteracted by reduction in pH by reducing the amount of positive ions in the aqueous solution. In an embodiment of the present invention, the pH of the aqueous solution that is distilled in step (e) is adjusted during the ion reducing step (d).

In step (e) of the present process, the reduced ion aqueous solution is distilled by applying vacuum and heat to the reduced ion aqueous solution to form an aqueous distillation product comprising 3-hydroxypropionic acid. The use of "more gentle" distillation techniques involving application of vacuum and lower levels of heat than would otherwise be required in distillation process undertaken at standard pressure is advantageous because it reduces the likelihood of formation of undesired side reactants in the recovery process. In embodiments, the distillation step (e) comprises heating the reduced ion aqueous solution to a temperature of from about 100° C. to about 200° C.; or from about 120° C. to about 180° C., or from about 130° C. to about 170° C., or from about 130° C. to about 150° C. In embodiments, the distillation step (e) is carried at a pressure of from about 0.5 to about 50 mm Hg absolute, or at a pressure of from about 5 to about 40 mm Hg absolute, at a pressure of from about 10 to about 35 mm Hg absolute.

Distillation by exposing the reduced ion aqueous solution to elevated temperature for relatively short times is also advantageous for reducing the likelihood of formation of undesired side reactants in the recovery process. In embodiments, the distillation step (e) is carried out by heating the reduced ion aqueous solution at a temperature above 100° C. for a time less than five minutes, or at a temperature above 120° C. for a time less than three minutes, or at a temperature above 130° C. for a time less than two minutes.

In embodiments, the distillation step (e) may be carried out by short residence time distillation techniques. In embodiments, the distillation step (e) is carried out by equipment selected from wiped film evaporation equipment, rising film evaporator equipment, thin film evaporation equipment, (centrifugal) molecular distillation equipment, falling film distillation equipment, or combinations, thereof. See a general discussion of such equipment in U.S. Pat. No. 7,560,579.

The concentration of 3-hydroxypropionic acid in the reduced ion aqueous solution prior to distillation of step (e) may have an impact on the presence of one or more undesirable side products or other impurities in the final concentrated product. In an embodiment, the concentration of 3-hydroxypropionic acid in the reduced ion aqueous solution prior to distillation of step (e) is from about 20 percent by weight to about 80 percent by weight. In another embodiment, the concentration of 3-hydroxypropionic acid in the reduced ion aqueous solution prior to distillation of step (e) is from about 25 percent by weight to about 70 percent by weight. In another embodiment, the concentration of 3-hydroxypropionic acid in the reduced ion aqueous solution prior to distillation of step (e) is from about 30 percent by weight to about 60 percent by weight.

In an embodiment of the present invention, the distillation step (e) is preferably carried out at a pressure of from about 20 to about 35 mm Hg absolute and a temperature of from about 130° C. to about 150° C. at a 3-hydroxypropionic acid concentration of from about 30 percent by weight to about 60 percent by weight.

In step (f) of the present process, the aqueous distillation product is recovered that comprises 3-hydroxypropionic acid typically at a concentration of at least thirty percent by weight of the aqueous distillation product, wherein the aqueous distillation product typically comprises less than five parts by weight acrylic acid per one hundred parts by weight 3-hydroxypropionic acid present. In embodiments, the 3-hydroxypropionic acid is recovered in step (f) at a concentration of at least about thirty-five percent by weight of the aqueous distillation product, or at a concentration of at least about forty percent by weight of the aqueous distillation product. In embodiments, the aqueous distillation product recovered in step (f) contains less than about three parts by weight acrylic acid per one hundred parts by weight 3-hydroxypropionic acid present, or less than about 1 part by weight acrylic acid per one hundred parts by weight 3-hydroxypropionic acid, or less than about 0.5 parts by weight acrylic acid per one hundred parts by weight 3-hydroxypropionic acid.

In embodiments of the present invention, the concentration of 3-hydroxypropionic acid in the aqueous distillation product comprising 3-hydroxypropionic acid recovered in step (f) is from about 30 percent by weight to about 80 percent by weight; or is from about 30 percent by weight to about 70 percent by weight; or is from about 30 percent by weight to about 60 percent by weight.

It will be noted that over time in storage, 3-hydroxypropionic acid may tend to react, for example to form dimers and trimers. The concentration of 3-hydroxypropionic acid that is recovered in step (f) is determined immediately after completion of the recovery process, prior to storage that may result in reactions of 3-hydroxypropionic acid that would change the determination of recovery concentration.

Combinations of the specific embodiments of each of the steps (a)-(f) as identified above are additionally contemplated. For example (and without limiting the contemplated combination of the various specific embodiments), in a particularly advantageous embodiment of the present invention, the method comprises the steps wherein the total sulfate ion and phosphate ion concentration is reduced to less than about 5000 ppm in step (d); the concentration of 3-hydroxypropionic acid in the aqueous distillation product of step (e) is from about 30 percent by weight to about 60 percent by weight; and the aqueous distillation product recovered in step (f) contains less than about 1 part by weight acrylic acid per one hundred parts by weight 3-hydroxypropionic acid. In another particularly advantageous embodiment of the present invention, the method comprises the steps wherein the total sulfate ion and phosphate ion concentration is reduced to less than about 3000 ppm in step (d); the concentration of 3-hydroxypropionic acid in the aqueous distillation product of step (e) is from about 30 percent by weight to about 60 percent by weight; and the aqueous distillation product recovered in step (f) contains less than about 0.5 part by weight acrylic acid per one hundred parts by weight 3-hydroxypropionic acid.

In another particularly advantageous embodiment of the present invention, the method comprises the steps wherein:
the total sulfate ion and phosphate ion concentration is reduced to less than about 3000 ppm in step (d);
the concentration of 3-hydroxypropionic acid in the reduced ion aqueous solution prior to distillation of step (e) is from about 30 percent by weight to about 60 percent by weight;
the distillation step (e) comprises heating the reduced ion aqueous solution to a temperature of from about 130° C. to about 150° C.;
the distillation step (e) is carried out at a pressure of from about 10 to about 35 mm Hg absolute; and
the aqueous distillation product recovered in step (f) contains less than about 0.5 parts by weight acrylic acid per one hundred parts by weight 3-hydroxypropionic acid.

In an embodiment of the present invention, the method further comprises new steps (j) of recovering a distillation bottom stream from distilling step (e), the distillation bottom stream comprising from about 5 percent to about 20 percent 3-hydroxypropionic acid of the total amount of the 3-hydroxypropionic acid present in the reduced ion aqueous solution of step (d);
(k) applying vacuum and heat to the distillation bottom stream; and
(l) recovering a second aqueous distillation product comprising 3-hydroxypropionic acid, wherein the second aqueous distillation product comprises less than about 3 part by weight acrylic acid per one hundred part by weight 3-hydroxypropionic acid present in the second aqueous distillation product.

This embodiment provides enhanced recovery of 3-hydroxypropionic acid from the aqueous distillation product by not requiring aggressive distillation conditions to be applied to the entire reduced ion aqueous solution. Additionally, more total 3-hydroxypropionic acid is recovered from the reduced ion aqueous solution to be distilled as compared to a like process where only one distillation step is carried out. In an embodiment, water is added to the distillation bottom stream prior to step (k). This embodiment enhances overall recovery of 3-hydroxypropionic acid by making it easier to recover 3-hydroxypropionic acid from the second distillation step.

It should be noted that a great portion of the water present in the reduced ion aqueous solution that is distilled in step (e) is removed with the 3-hydroxypropionic acid that is recovered in step (f), and therefore the distillation bottom stream initially has a relatively high 3-hydroxypropionic acid. Dilution of the distillation bottom stream with water helps reduce formation of undesired side reactants or impurities during the second distillation, and additionally assists in efficient performance of the second distillation operation.

In another embodiment of the present invention, the method further comprises prior to the distilling step (e) the new step (g) of increasing the concentration of 3-hydroxypropionic acid in the reduced ion aqueous solution of step (d) to from about 30 percent by weight to about 70 percent by weight of the solution by evaporating a portion of the liquid present in the reduced ion aqueous solution at a solution temperature of from about 60° C. to about 100° C. As above, this low heat increase of concentration of 3-hydroxypropionic acid is particularly advantageous in providing both an economic process and also in reducing introduction of undesired side products or impurities. In an embodiment, the evaporation of liquid takes place at a solution temperature of from about 70° C. to about 90° C. In an embodiment, the evaporation of liquid takes place at a pressure of from about 250 to about 300 Torr.

In another embodiment of the present invention, the method further comprises the new step (h) of reducing the amount of micro-organism cells present in the fermentation broth prior to step (d). In an embodiment, the reducing step (h) takes place prior to the acidifying step (c). In an embodiment, the reducing step (h) is carried out by use of a separator device selected from a centrifuge, a belt filter, a drum filter, and a membrane filter.

FIG. 1 is a process flow diagram of one embodiment of the present method. As shown, a fermentation broth is provided, and cells are removed therefrom. Water is removed by a first evaporation step and the fermentation broth is acidified to form an aqueous solution comprising 3-hydroxypropionic acid. Gypsum is removed and the total sulfate ion and phosphate ion concentration of the aqueous solution is reduced using ion exchangers. The reduced ion aqueous solution comprising 3-hydroxypropionic acid is subjected to a second evaporation step to remove water, and the reduced ion aqueous solution is subjected to two distillation steps.

In the first evaporation step described above, the concentration of 3-hydroxypropionic acid and/or salts thereof are after the completion of the first evaporation step typically less than 350 grams 3-hydroxypropionic acid equivalents per liter.

EXAMPLES

Representative embodiments of the present invention will now be described with reference to the following examples that illustrate the principles and practice of the present invention.

The following analytical methods and sample preparations were used in the examples below.

Analytical Method For 3-HP

3-Hydroxypropionic acid (3-HP), acrylic acid, and various other organic acids, alcohols, and sugars in the samples are analyzed using high performance liquid chromatography (HPLC). This HPLC method utilizes a combination of two BioRad Aminex HPX-87H columns, in conjunction with Refractive Index (RI) detection and Ultraviolet (UV) detection at 210 nm. The RI detector is for the quantification alcohols and sugars, and the UV detector for all the organic acids. Standards and samples are prepared by mass in volumetric flasks diluted with the mobile phase. No internal standard is used. Results were calculated in weight %.

The HPLC is a Waters Alliance 2695 modular High Performance Liquid Chromatography system that includes a pump, auto-sampler, solvent in-line gasser, and column heater. The RI detector is a Waters 2410 Refractive Index Detector, and the UV detector a Waters 2487 Dual Wavelength Ultraviolet Detector. The columns are Aminex HPX-87H 300×7.8 mm columns (BioRad), used with a Security Guard cartridge holder (Phenomenex) and Carbo H+ guard cartridges (Phenomenex).

An Isocratic mobile phase of 10 mM $H_2SO_4$ in high-purity water, containing sodium azide (0.005%), filtered through an 0.45 micron filter, is used at a flow rate of 0.5 mL/min. The column temperature is 55° C. Sample injection volume is 20 µL. Each run is 60 minutes long. The internal temperature of the Refractive index detector is 35° C. 18+ megaohm ultrapure water is used.

Standard Stock Solution 1 containing Glucose (0.1 g/L), Malic acid (0.1 g/L), Pyruvic acid (0.1 g/L), Arabitol (0.1 g/L), Succinic acid (0.1 g/L), Lactic acid (0.1 g/L), Glycerol (0.1 g/L), and Acrylic acid (0.1 g/L) in 10 mM $H_2SO_4$ is prepared. The stock solution is stored in a refrigerator, and diluted 10:1 with 10 mM $H_2SO_4$ solution to prepare the Standard 1 working solution for HPLC analysis. Standard 3-HP (5 g/L) is prepared in 10 mM $H_2SO_4$ solution. This is the 3-HP working standard solution for HPLC analysis.

For sample preparation, 0.25 grams of sample is weighed into a 25-ml volumetric flask and diluted with 10 mM sulfuric acid and filtered through a 0.45 micron nylon syringe filter. The wt. % of alcohols including glycerol and sugars are calculated using Refractive Index (RID) peak areas. The wt. % of organic acids is calculated using UV peak area.

The phosphate and sulfate ions are determined by measuring elemental sulfur and phosphorous by inductively coupled plasma atomic emission spectroscopy (ICP) analysis. Analysis was done using a Spectro Arcos FHS12 instrument. All sulfur and phosphorous is believed to be in the form of sulfate and phosphate ions, respectively.

General Procedures For Examples 1 through 8:

3-HP Fermentation Broth

3-HP broth produced by fermentation from glucose in yeast is used as the starting material for the processing steps. The fermentation broth contains 37 g/L 3-HP in addition to other fermentation by-products including unfermented sugars, other organic acids such as lactic, pyruvic, succinic, and salts. Some of the major components are shown in Table 1 below. Yeast biomass is also removed from the broth using bench top centrifugation (2200×g for 5 minutes) and then the supernatant is decanted.

TABLE 1

Typical concentrations of major components of the aqueous 3-HP fermentation broth.

| Component | Concentration (g/L) |
| --- | --- |
| 3-HP | 35 |
| Unfermented sugars | 1 |
| Organic acids | 3 |
| Calcium | 6 |
| Phosphate | 4 |
| Glycerol | <10 |
| Typical pH | 2-5 |

Acidulation

The calcium in the broth is removed by adding concentrated $H_2SO_4$ until the pH of the broth solution is between 2-2.5. The precipitated gypsum is removed using bench top centrifugation (2200×g for 5 minutes) and the supernatant is then decanted.

Ion Exchange (Demineralization)

The acidulated fermentation broth goes through a demineralization step using cation and anion exchange. Cation exchange is done using AMBERLITE IR120 Strong Acid Cation Exchanger resin, available from Rohm and Haas. The resin is loaded in a 1" internal diameter column with an approximate bed volume of 200 ml. The column is conditioned by passing 200 ml of 1M HCl through the column followed by DI water until the effluent pH is above 5. The cation column is used to reduce the amounts of calcium, sodium, potassium, iron and magnesium. 3-HP broth is passed through the column until breakthrough conditions (cation resin capacity is exceeded) are reached indicated by a rise in pH in the effluent stream. Depending on the ionic loading, 1-10 L of broth is passed through the column.

The effluent from the cation exchange is then passed through anion exchange column. The anion exchange resin is DOWEX MARATHON WBA Weak Base Anion Exchange resin available from The Dow Chemical Company. The resin is loaded in a 1" internal diameter column with an approximate bed volume of 200 ml. The column is conditioned by passing 200 ml of 1M NaOH through the column followed by DI water until the effluent pH is below 8. The anion column is used to reduce the amounts of sulfate, phosphate and chloride ions. 3-HP cation exchange effluent is passed through the column until breakthrough conditions (anion resin capacity is exceeded) are reached indicated by a drop in pH in the effluent stream. Depending on the ionic loading, 0.5-2 L of broth are passed through the column.

Evaporation/Concentration

The material is concentrated using a rotary evaporator to a 3-HP concentration of 550-650 g/L. The pressure is set at 50 torr and the temperature increases from 40 to 60° C. as the material becomes more concentrated. The concentration step can take place before and/or after the demineralization steps.

Distillation

Distillation was carried out using a short path wiped film evaporator (model KDL4 manufactured by UIC). Material is fed from the top of the unit down to the heated surface. The evaporator, with a total surface area of 0.043 $m^2$, is a jacketed borosilicate glass cylinder and uses hot oil to control temperature. Inside the heated surface, Teflon rollers are used to distribute the feed material. For feed rates of 4-7 ml/min, the residence time or contact time of the feed material to the heated surface is approximately 30-60 seconds. An internal condenser located in the center of the heated surface is used to condense the distillate phase which is collected in a receiver flask. The non-volatile bottoms are collected in a separate receiver flask. The feed rate is controlled by a peristaltic pump. Feed rates are measured by measuring the weights of the feed flask over time. Typical feed weights are around 50-100 g. In the following examples, the feed rate, jacket temperature, and vacuum pressure are controlled. All pressures are absolute. Unless otherwise indicated, reported distillation temperatures are jacket temperatures.

Example 1 (Comparative)

This example shows the effect of having a high combined sulfate and phosphate concentrations (for example, above 100,000 ppm) in the reduced ion aqueous solution of 3HP feeding the distillation results in a recovered distillate with a high content of acrylic acid (for example, greater than 30 parts Acrylic Acid per 100 parts 3HP).

3-HP broth is prepared as described above in the General Procedure. The fermentation broth has a pH of 4 and contains 37 g/L 3HP, 5927 ppm calcium, 243 ppm sulfate, and 8946 ppm phosphate. The fermentation broth undergoes cell separation by centrifugation. The broth is then acidified with concentrated sulfuric acid to pH of 2 and then clarified using centrifugation to remove gypsum and other un-dissolved solids. The calcium concentration of the acidified and clarified broth is 524 ppm. The broth is demineralized using cation and anion exchange columns. The sulfate concentration is reduced to 1583 ppm and the phosphate concentration is reduced to 5998 ppm with a 3HP concentration close to 35 g/L. The resulting 3HP solution is then concentrated by evaporation to 638 g/L which also increased the sulfate concentration to 33466 ppm and phosphate concentration to 95473 ppm.

The reduced ion aqueous solution of 3HP is then distilled using the wiped film evaporator (WFE). The distillation conditions are shown in Table 1-1 which also summarizes the relation between the distillation feed, conditions and acrylic acid formation.

TABLE 1-1

Distillation conditions using Wiped Film Evaporator. Recovery is calculated as the amount of 3-HP collected in the distillate stream compared to the 3-HP fed into the WFE. Both 3-HP and Acrylic Acid concentrations are given along with the parts Acrylic Acid per 100 parts 3HP. $SO_4^{2-}$ and $PO_4^{3-}$ concentrations are calculated from sulfur and phosphorous measured by ICP, respectively.

| | Distillation Parameters | | | Feed Concentration | | | Distillate Profile | | | |
|---|---|---|---|---|---|---|---|---|---|---|
| ID | Temp (° C.) | Pres (torr) | Feed (g/min) | 3HP (g/L) | SO4 (ppm) | PO4 (ppm) | Recovery (%) | [3-HP] (g/L) | [AA] (g/L) | Parts Acrylic Acid per 100 Parts 3HP |
| Ex1 | 180 | 20 | 6 | 638 | 33466 | 95473 | 12% | 235 | 91 | 39.1 |

Example 2

This example shows the effect of lowering the combined sulfate and phosphate concentrations (for example, below 15,000 ppm) in the reduced ion aqueous solution of 3HP fed into distillation results in a recovered distillate with lower acrylic acid formation (for example, below 3 parts per 100 parts 3HP).

3-HP broth is prepared as described above in the General Procedure. The fermentation broth has a pH of 4 and contains 37 g/L 3HP, 4409 ppm calcium, 224 ppm sulfate, and 7654 ppm phosphate. The fermentation broth undergoes cell separation by centrifugation. The broth is then acidified with concentrated sulfuric acid to pH of 2 and then clarified using centrifugation. The calcium concentration of the acidified and clarified broth is 427 ppm. The broth is demineralized using cation and anion exchange columns. The resulting 3HP solution is then concentrated by evaporation to approximately 600 g/L 3HP which also results in sulfate concentration of 30025 ppm and phosphate concentration of 22241 ppm. The concentrated solution is demineralized a second time by passing through cation and anion exchange columns again. The resulting concentrated solution has a sulfate concentration of 1972 ppm and phosphate concentration of 11477 ppm with a 3HP concentration of 556 g/L.

The prepared broth is then distilled using the wiped film evaporator (WFE). The distillation conditions are shown in Table 2-1 which also summarizes the relationship between the distillation feed, conditions and acrylic acid formation.

Example 3

This example shows the recovery of 3HP on a larger scale going through the process of cell removal, acidulation, ion exchange and distillation. The reduced ion aqueous solution of 3HP has a lower combined sulfate and phosphate concentration (for example, below 2000 ppm).

3HP is prepared as described in the General Procedure. The fermentation broth undergoes cell separation by membrane filtration using a ceramic membrane with a 0.1 micron pore size. The broth is acidified with concentrated sulfuric acid to pH of 2.6 and is then clarified using a filter. The broth is demineralized using cation and anion exchange columns and then concentrated up to 37.2% monomer 3HP by evaporation. The reduced ion aqueous solution having a phosphate and sulfate concentration of 1088 ppm and 459 ppm, respectively, feeds into a rising film evaporator (RFE) for distillation.

The RFE is a single tube (1.5"×20') with a steam jacket. The feed is pumped to the bottom of the tube where the 3HP, water and other volatile components vaporize and carry over to an external condenser where the distillate stream condenses and is collected. The material that does not volatilize flows over the top of the RFE and is collected separately as a bottoms residue. For this example, the feed rate is set at 75 g/min resulting in a residence time in the heated tube of approximately 90 seconds. The vacuum pressure is set at 27 torr and the steam pressure in the jacket is set to 75 psig, resulting in an RFE wall temperature of 160° C.

TABLE 2-1

Distillation conditions using Wiped Film Evaporator. Recovery is calculated as the amount of 3-HP collected in the distillate stream compared to the 3-HP fed into the WFE. Both 3-HP and Acrylic Acid concentrations are given along with the parts Acrylic Acid per 100 parts 3HP. $SO_4^{2-}$ and $PO_4^{3-}$ concentrations are calculated from sulfur and phosphorous measured by ICP, respectively.

| | Distillation Parameters | | | Feed Concentration | | | Distillate profile | | | |
|---|---|---|---|---|---|---|---|---|---|---|
| ID | Temp (° C.) | Pres (torr) | Feed (g/min) | 3HP (g/L) | SO4 (ppm) | PO4 (ppm) | Recovery (%) | [3-HP] (g/L) | [AA] (g/L) | Parts Acrylic Acid per 100 Parts 3HP |
| Ex2 | 180 | 20 | 6.5 | 556 | 1972 | 11477 | 75% | 673 | 8.5 | 1.31 |

TABLE 3-1

Distillation conditions using Rising Film Evaporator. Recovery is calculated as the amount of 3-HP collected in the distillate stream compared to the 3-HP fed into the RFE. Both 3-HP and Acrylic Acid concentrations are given along with the parts Acrylic Acid per 100 parts 3HP. $SO_4^{2-}$ and $PO_4^{3-}$ concentrations are calculated from sulfur and phosphorous measured by ICP, respectively.

| | Distillation Parameters | | | Feed Concentration | | | Distillate profile | | | Parts Acrylic Acid per |
|---|---|---|---|---|---|---|---|---|---|---|
| ID | Temp (° C.) | Pres (torr) | Feed (g/min) | 3HP (wt %) | SO4 (ppm) | PO4 (ppm) | Recovery (%) | [3-HP] (wt %) | [AA] (wt %) | 100 Parts 3HP |
| Ex3 | 160 | 27 | 75 | 37.2 | 459 | 1088 | 77% | 66 | 0.03 | 0.04 |

This data shows 3HP can be recovered with a very low Acrylic Acid content (below 1 part in 100 3HP, and even below 0.5 parts in 100 parts 3HP) when the combined sulfate and phosphate concentration in the reduced ion aqueous solution feeding the distillation is low.

Example 4

This example shows additional 3HP can be recovered by distilling the bottoms residue from the first distillation in Example 3.

The bottoms residue collected from Example 3 is distilled using a wiped film evaporator as described in the General Procedure. This bottoms stream is 5-6 times more concentrated in sulfates and phosphates compared to the reduced ion aqueous 3HP solution that feeds the RFE in Example 3, as the majority of the more volatile water and 3HP is collected in the distillate stream. The material is fed into the WFE at a rate of 5 g/min at a pressure of 1 torr and jacket temperature of 180° C. The second distillate stream collected contains 507 g/L 3HP and 12.9 g/L acrylic acid (2.5 parts acrylic acid per 100 parts of 3HP). The total 3HP recovery increases from 77% (single RFE distillation) to 84% (combined RFE and WFE) based on the reduced ion aqueous solution.

Example 5

This example demonstrates the effects of distillation time, temperature, 3HP concentration, and anion concentration on the length of time of distillation that can be used without creating high quantities of acrylic acid.

In this example, 3HP broth is prepared through the Evaporation/Concentration step as described in the General Procedure. Following the Ion Exchange step of the General Procedure, the 3HP concentration in the reduced ion aqueous solution is 30% by weight. The Ion Exchange step is performed at two different conditions. In one case the total sulfate and phosphate concentration is reduced to 3,000 ppm, and in the second case is reduced to 10,000 ppm. The material is then concentrated to different levels as described in the Evaporation/Concentration step of the General Procedure to three different levels of 3HP concentration.

Table 5-1 shows typical parameters of concentration of 3HP, the combined sulfate and phosphate level in the reduced ion aqueous solution feeding the distillation, and the time at elevated temperatures in distillation that are believed will result in an acrylic acid formation of less than 1 part per 100 parts 3HP in the distillate.

TABLE 5-1

| Distillation Temperature (Degrees C.) | 3HP Concentration (g/L) | SO4 + PO4 (ppm) | Allowed Time (min) |
|---|---|---|---|
| 140 | 500 | 5,000 | 3 |
| 150 | 600 | 6,000 | 1.5 |
| 130 | 300 | 10,000 | 4 |

By performing distillation at lower 3HP concentrations, the rate of acrylic acid is reduced. Additionally, the boiling point of the reduced ion aqueous solution is lower at lower 3HP and concentrations, so that the temperature at which distillation can be carried out for comparable recoveries is lower. These lower temperatures further reduce the rate of acrylic acid formation.

Example 6

This example shows the effect of temperature in distillation on the acrylic acid formed.

3-HP broth is prepared as described above in the General Procedure. The fermentation broth has a pH of 4 and 37 g/L 3HP. The fermentation broth undergoes cell separation by centrifugation. The broth is evaporated to reach a concentration of 220 g/L 3HP resulting in a sulfate concentration of 2383 ppm and phosphate concentration of 7276 ppm. No acidulation is done in this example. A similar result to acidulating the broth is achieved by increasing the capacity of the cation exchange resin to remove the calcium ions that would be removed by acidulation. The broth is then demineralized through ion exchange which reduces the sulfate concentration to 461 ppm and phosphate concentration of 124 ppm. The 3HP solution is then concentrated to 577 g/L 3HP, 1755 ppm sulfate, and 472 ppm phosphate.

The prepared broth is then distilled using the wiped film evaporator (WFE). The distillation conditions are shown in Table 6-1, which also summarizes the relationship between the distillation feed, distillation conditions and acrylic acid formation.

TABLE 6-1

Distillation conditions using Wiped Film Evaporator. Recovery is calculated as the amount of 3-HP collected in the distillate stream compared to the 3-HP fed into the WFE. Both 3-HP and Acrylic Acid concentrations are given along with the parts Acrylic Acid per 100 parts 3HP. $SO_4^{2-}$ and $PO_4^{3-}$ concentrations are calculated from sulfur measured by ICP, respectively.

| | Distillation Parameters | | | Feed Concentration | | | Distillate profile | | | |
| --- | --- | --- | --- | --- | --- | --- | --- | --- | --- | --- |
| ID | Temp (° C.) | Pres (torr) | Feed (g/min) | 3HP (g/L) | SO4 (ppm) | PO4 (ppm) | Recovery (wt %) | [3-HP] (g/L) | [AA] (g/L) | Parts Acrylic Acid per 100 Parts 3HP |
| Ex6a | 160 | 20 | 5 | 577 | 1755 | 472 | 85% | 669 | 1.4 | 0.21 |
| Ex6b | 170 | 20 | 5 | 577 | 1755 | 472 | 78% | 681 | 3.2 | 0.45 |
| Ex6c | 180 | 20 | 5 | 577 | 1755 | 472 | 68% | 608 | 5.2 | 0.84 |

The results show temperatures below 180° C. (e.g. 160° C. and 170° C.) results in Acrylic Acid formation less than 0.5 parts per 100 parts 3HP (i.e. wt % acrylic acid less than 0.5 wt %)

Example 7

This example is similar to Example 4 and shows the amount of acrylic acid formed in the second distillate stream is lowered as compared to Example 4 by adding additional water to the feed of the second distillation.

Water is added to the Bottoms residue generated in Example 3 to increase the water concentration to 20 wt %. This diluted stream feeds into a WFE distillation at 5 g/min. The WFE operates at 160° C. and 20 torr. The resulting second distillate has a 1.1 parts Acrylic Acid per 100 parts 3HP.

Example 8 (Comparative)

This example shows how large amounts of acrylic acid is generated with long exposure time to heat.

The same 3-HP broth prepared and used in Example 6 is used in this example, except for the final WFE distillation. Instead, a batch distillation experiment is set up using a 500 ml round bottom flask to hold the material. The flask is placed in an electric heating mantle to provide heat. Above the flask is an adapter to connect the condenser (water cooled) which allows the vapor to cool and collect in a separate distillate collection flask. A thermometer is placed at the adaptor to measure the temperature of the vapor just before entering the condenser. The setup is connected to a vacuum pump set at 20 torr.

200 g of the prepared broth is added to the flask and heating mantle is turned on. Heating takes approximately 2 hours to reach a liquid temperature of approximately 150° C. At that point condensate starts collecting in the distillate collection flask and the vapor temperature reaches 140° C. Distillation continues for 30 minutes at which time the vacuum is shut off and the heating mantle is removed. 83.6 g of distillate is collected and 116.5 g of bottoms is collected. Table 8-1 shows the composition of the 3 streams.

TABLE 8-1

| Sample | 3HP (g/L) | Acrylic (g/L) | 3HPRecovery | Parts Acrylic Acid to 100 Parts 3HP |
| --- | --- | --- | --- | --- |
| Feed | 577 | ND* | | |
| Distillate | 184 | 12 | 13% | 6.6 |
| Bottoms | 887 | 11 | | 1.1 |

*ND indicates not detectable by HPLC.

Example 9

This example shows a large scale fermentation process for producing fermentation broth containing 3HP and/or salts thereof.

A 3HP producing yeast strain is employed in a fermentation to produce 3HP and/or salts thereof. Fermenters are inoculated with biomass grown in defined medium see Tables 9-1, 9-2 and 9-3. 3HP producing yeast strains are multiplied (i.e. grown) in a 10,000 liter (L) aerobic seed fermentor. The resulting yeast producing strains are inoculated into a 1,000,000 liter production fermenter to provide an initial cell dry weight of 0.1 g/L. The fermenter media at the time of inoculation is outlined in Table 9-1. During the fermentation, pH is controlled at 4.0 by addition of an aqueous suspension of 30% $Ca(OH)_2$ (lime). The production fermenter is sparged at 0.1 VVM (standard volume of air sparged per volume of the fermentor per minute) with air. Agitation is provided to the production fermenter to achieve an oxygen uptake rate (OUR) of 14 mmol/(L*h). The fermentation is operated so that after the cells achieve a sufficient density, oxygen limitation is achieved and subsequently maintained throughout the rest of the fermentation (e.g., dissolved oxygen less than about 10% of air saturation at 1 atm). Dissolved oxygen during the fermentation is measured using Mettler Toledo INPRO® 6800 sensor (Mettler-Toledo GmbH, Urdorf, Switzerland).

TABLE 9-1

Defined Media for production fermenters

| Compound | Concentration (g/kg) |
| --- | --- |
| $C_6H_{12}O_6$ | 107 g/l initial glucose |
| Urea | 1.7 |

TABLE 9-1-continued

Defined Media for production fermenters

| Compound | Concentration (g/kg) |
|---|---|
| $KH_2PO_4$ | 1.5 |
| $MgSO_4$—$7H_2O$ | 0.25 |
| 1000x Vitamin Solution | 1 |
| 1000x Trace Solution | 1 |

TABLE 9-2

1000X Trace Solution.

| Chemical | g/1.0 L |
|---|---|
| $C_{10}H_{14}N_2Na_2O_8 \cdot 2H_2O$ | 15.00 |
| $ZnSO_4 \cdot 7H_2O$ | 4.50 |
| $MnCl_2 \cdot 4H_2O$ | 1.00 |
| $CuSO_4 \cdot 5H_2O$ | 0.30 |
| $FeSO_4 \cdot 7H_2O$ | 3.00 |

TABLE 9-3

1000X Vitamin Solution

| Chemical | g/1.0 L |
|---|---|
| Biotin (D-) | 0.05 |
| Ca D(+) panthotenate | 1.0 |
| Nicotinic acid | 5.0 |
| Myo-inositol (for microbiology) | 25.0 |
| Thiamine hydrochloride | 1.0 |
| Pyridoxine hydrochloride | 1.0 |
| p-Aminobenzoic acid | 0.20 |

Cell concentration at the time of inoculation and at the end of fermentation is obtained from an optical density measurement using an established conversion factor between dry cell mass and optical density. Optical density is measured at a wavelength of 600 nm with a 1 cm pathlength using a model Genesys20 spectrophotometer (Thermo Scientific). Unless explicitly noted otherwise, an experimentally derived conversion factor of 2.3 OD600 units per 1 g dry cell mass is used to estimate cell dry weight.

OUR is calculated using methods known to those of skill in the art. For this example, Oxygen, Nitrogen and $CO_2$ values are measured by a Mass Spectrometer (Thermo Scientific).

The batch finishes and samples are taken at 40 h batch time and analyzed for biomass growth via OD600. Glucose and 3HP are measured by high performance liquid chromatography with refractive index detector. The final 3-hydroxypropionic acid equivalents (based on 3HP and/or salts thereof contained in the fermentation broth) concentration is 80 g/L, which equates to a volumetric productivity of 3HP of 2 g/(L*hr), and a yield of 0.75 g 3-hydroxypropionic acid equivalents per gram glucose and a cell dry weight of 7-10 g/L. Final sulfate and phosphate concentrations in the broth is 300 ppm and 200 ppm, respectively. In some instances, with an appropriate organism and fermentation parameters, the final 3HP equivalents concentration may be at least 100 g/liter (L), a volumetric productivity of 3HP of 2.5 g/(L*hr), and a yield of at least 0.75 g 3-hydroxypropionic acid equivalents per gram of glucose (in some instances at least 0.77 g 3-hydroxypropionic acid equivalents per gram of glucose), with a final cell dry weight of less than 10 g/L (preferably less than 5 g/L).

Example 10

This example shows the processing of 3HP and/or salts thereof produced from the fermentation of Example 9 using cell removal, evaporation, acidulation, clarification, and ion exchange.

Cell Removal: Referring to step 2 of FIG. 1, the fermentation broth from Example 9 is obtained and is fed into several centrifuges at a combined rate of 283 $m^3$/hr. The centrifuges each have a disc stack configuration where the cell free fermentation broth containing 3HP and/or salts thereof pass through to the product discharge. The cell concentrate underflow stream contains 40-50 volume percent cells based on the liquid present and discharges through ejection nozzles on each centrifuge. Concentrating the cells below 40% by volume of the discharge results in lower recovery of 3HP from the overall recovery process as a higher percentage of 3HP (and/or salts thereof) ends up in the cell concentrate discharge stream. Concentrating the cells above 50% typically causes the cell concentrate stream to be very viscous and difficult to handle. To improve the recovery of 3HP from the overall recovery process, additional water (2-3 times the volume of the cell concentrate stream) is mixed with the concentrate stream and the diluted volumetrically adjusted cell concentrate stream is fed into the inlet of another centrifuge. Additional cell free 3HP containing broth is discharged; and the cells are once again concentrated up to 40-50% vol % and discharges through the ejection nozzles on the centrifuge. To further improve 3HP recovery, the cell concentrate discharge from the $2^{nd}$ stage centrifuge is diluted with water (2-3 times by volume) and is processed through a $3^{rd}$ stage centrifuge. The three cell free 3HP containing broth streams are combined and then carried forward for further processing.

In order to reduce the amount of wash water used, a counter current wash system is employed. Fresh water combines with the cell concentrate stream exiting the $2^{nd}$ stage centrifuge and feeding the $3^{rd}$ stage centrifuge. The cell free discharge of the $3^{rd}$ stage centrifuge is used to dilute the cell concentrate discharge of the $1^{st}$ stage centrifuge and then feeds the $2^{nd}$ stage centrifuge. After cell separation, the concentration of 3HP (and/or salts thereof) drops to between 90-95% of the starting concentration of the 3HP and/or salt thereof in the fermentation broth from Example 9, depending on how much wash water is used.

Evaporation: Referring to FIG. 1, step 3, the cell free 3HP containing combined broth is evaporated to raise the concentration of 3HP (and/or salts thereof). The broth feeds into a mechanical vapor recompression (MVR) evaporator to remove water from the broth. Mechanical vapor recompression evaporator and other types of evaporators that utilize vapor compression to remove water from a liquid material and therefore concentrate the amount of 3HP (and salts thereof) that are contained in a liquid. If thermal heat such as steam is readily available, evaporators that use thermal heat (with or without vacuum) can also be used. An example of an evaporator that uses thermal heat from a source such as steam to concentrate the 3HP equivalents in a broth are shell-in-tube evaporators (such as forced recirculation and falling film evaporators). Also, evaporators that utilize both mechanical vapor recompression and thermal heat cycle(s) from sources such as steam, or heated fluid (such as oil) may be effectively utilized. Two stages of MVR evaporation are used and operate at 60-80° C. and 260-300 mm Hg. The concentrated broth exits the evaporator at 240 g/L 3HP equivalents.

It is also possible to concentrate the fermentation broth using evaporation prior to the cell separation step. Concentrating the broth before the cell separation step reduces the total volume of broth feeding into the centrifuge and does not require as many centrifuge units given the smaller hydraulic loading of the evaporated broth. Cell removal and evaporation are typically carried out before the acidulation. It is believed that the concentration of the 3HP and/or salts thereof in the fermentation broth and absence of cells allows for more efficient acidulation and processing after acidulation, such as gypsum removal.

Acidulation: Referring to FIG. 1, step 4, sulfuric acid is added to evaporated concentrated 3HP containing broth to lower the pH and convert most of the calcium salts of 3HP to the free acid form. The $CaSO_4$, formed (also known as gypsum) precipitates out of solution. In a large agitated batch reactor, the sulfuric acid is added slowly to the concentrated 3HP containing broth, over the period of 15-25 minutes to slowly form gypsum precipitate. The sulfuric acid is added until the concentrated broth reaches a pH of 1.7-1.8.

The acidulation step can be run as a batch or continuous process. Operating a continuous acidulation process has the advantage of processing larger volumes of concentrated 3HP containing broth without the need for an array of acidulation tanks. As an example of a continuous acidulation step, for a broth flow of 115 m$^3$/hr, the acidulation tank typically has a volume greater than 40 m$^3$, typically requiring a residence time of at least 20 minutes. The dosing rate of sulfuric acid is controlled so the pH of the solution is between 1.6 and 1.8.

Clarification to remove gypsum: Referring to FIG. 1, step 5, the acidulated 3HP broth containing gypsum particles is next clarified to remove gypsum. Combined with the acidulation step, the clarification step removes over 95% of the calcium in the broth prior to acidulation. The slurry of acidulated 3HP broth containing gypsum is fed onto a belt filter to filter out the gypsum particles. A filter cake of gypsum forms on top of the filter as the filtrate permeates the cake and filter. A vacuum is applied to the belt to help draw the broth through the filter. The gypsum cake does contain residual 3HP broth. Therefore, to increase the recovery of 3HP, water is sprayed on the gypsum cake washing the broth away from the cake as filtrate. To further increase recovery of 3HP, an additional stage of washing is performed and the filtrate is collected. To reduce the amount of wash water used, a counter current wash system is employed. Fresh water is applied to the $2^{nd}$ wash stage. The filtrate of that wash is used in the $1^{st}$ wash stage.

The gypsum cake thickness is typically maintained at 1 inch or thinner so that the filtrate can readily permeate the cake and filter. As the concentration of the 3HP in the evaporated fermentation broth feeding the acidulation step increases, the permeation or flux rate of 3HP through the gypsum cake decreases. Table 10-1 shows the correlation between the 3HP equivalents concentration feeding acidulation and the resulting flux rate of broth through the filter. Typically, the evaporation step before the acidulation step is carried out in a manner that provides a broth concentrated in 3HP equivalents, wherein the 3HP equivalent concentration is below 350 g/L, preferably below 330 g/L.

TABLE 10-1

Flux rate of the broth through the filter cake when acidification step is carried out on concentrated broths containing differing 3HP equivalents concentration. Cake thickness is close to 1 inch thick. Flux is measured as ml of broth filtered per minute per minute per cm$^2$ of surface area filter.

| 3HP equivalents (g/L) | Flux (ml/min/cm$^2$) |
|---|---|
| 99 | 2.6 |
| 158 | 2.4 |
| 199 | 1.7 |
| 231 | 0.8 |
| 279 | 0.2 |
| 356 | <0.05 |

As can be seen from Table 10-1, the 3HP equivalent concentration of the broth just prior to acidulation preferably is less than 330 grams 3HP equivalents/liter broth.

Other filtration devices such as a press filter or centrifuge could also be used to carry out the removal of gypsum (i.e. clarification step).

Demineralization/ion exchange: Referring to FIG. 1, step 6, the clarified 3HP broth is next treated to reduce the total sulfate ions and phosphate ions present in the broth to produce a reduced ion aqueous solution. The broth is passed through a cation exchange column first to remove residual calcium as well as other cations such as potassium and manganese. As the capacity of the cation resin is consumed, some of the cations begin to breakthrough and exit with the effluent 3HP containing solution. When this happens, water is fed through the column to elute out residual 3HP in the column. The column is then regenerated with HCl solution, rinsed with water, and then put back into service.

The 3HP effluent out of the cation column is then fed into an anion column where anions are removed, in particular phosphate and sulfate anions. Because the sulfate and phosphate concentrations can affect the subsequent distillation steps, it is desirable to control the concentration of sulfate and phosphate in the final output of the ion exchangers. Because of its charge density, phosphate ions tend to breakthrough first. When sulfate levels start to break through, water is fed into the column to elute out any residual 3HP. The column is regenerated with a solution of NaOH, rinsed with water, and then put back into service.

The properties of the reduced ion aqueous solution comprising 3HP that is obtainable from the above described demineralization described above are indicated in Table 10-2.

TABLE 10-2

Stream data for key components after each step of the 3HP recovery process described above in example 9 and 10.

|  | Fermentation | Cell Removal | Evaporation | Clarification | Demineralization |
|---|---|---|---|---|---|
| 3HP equivalents concentration | 80 g/L | 75 g/L | 240 g/L | 240 g/L | 220 g/L |
| Ca | 10000 ppm | 10000 ppm | 25000 ppm | 200-500 ppm | 20 ppm |
| Sulfate | 200 ppm | 200 ppm | 400-700 ppm | 5000-10000 ppm | 200 ppm |
| Phosphate | 300 ppm | 300 ppm | 500-800 ppm | 500-800 ppm | 500 ppm |
| pH | 4.1 | 4.1 | 4.1 | 1.7 | 1.7 |

Table 10-2 shows that a 3HP containing reduced ion aqueous solution can effectively be produced at large scale that has a total sulfate ion and phosphate ion concentration less than 3,000 ppm and in some instance less than 1000 ppm.

Example 11

Figure 2:
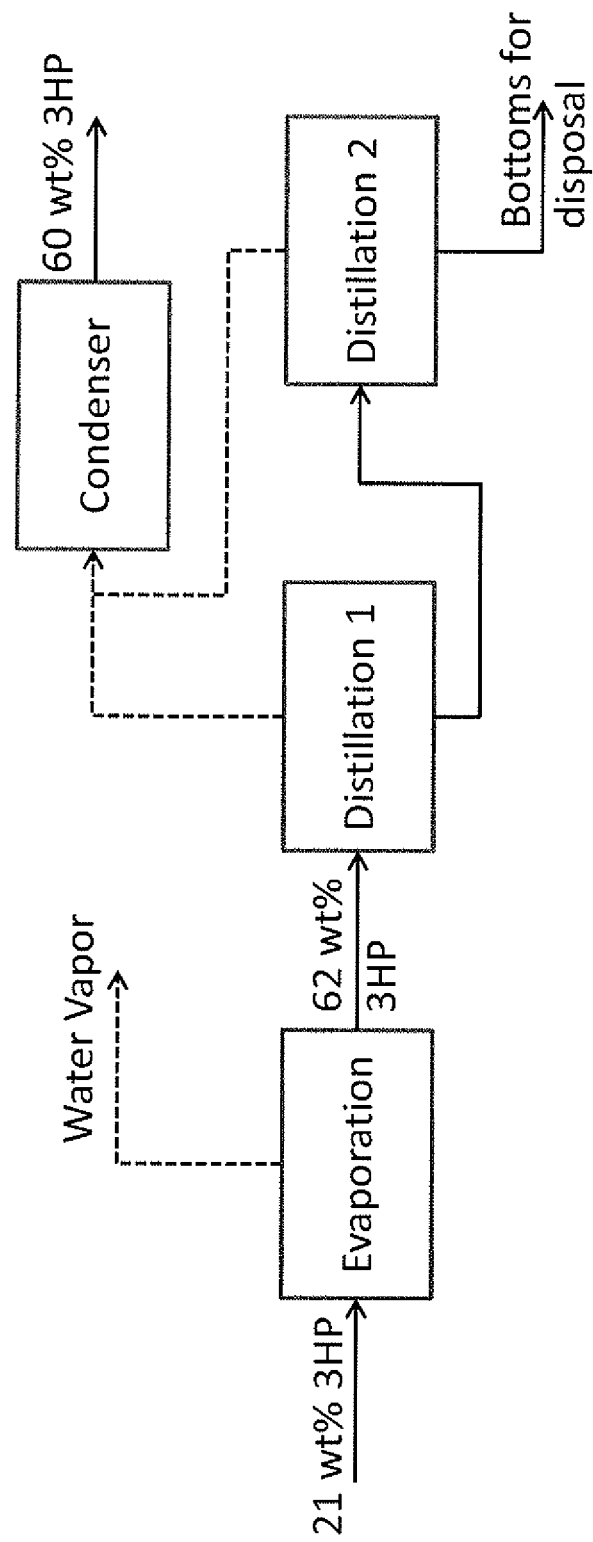
FIG. 2 is a process flow diagram depicting the processing steps described in Example 11.

Now referring to FIG. 2, in this example, the 3HP containing reduced ion aqueous solution from Example 10 is fed to a three stage thermal vapor recompression system. There, under the conditions of 0.39 bar pressure and each stage has a temperature of 80° C. to 85° C., the concentration of the reduced ion aqueous solution is increased from 21 wt % 3HP (220 g/L 3HP) to 62 wt % 3HP. Condensed water vapor from the evaporation process is recycled for use in fermentation and/or for flushing the demineralization.

The concentrated 3HP containing solution is then fed to a series of two distillation columns. In these columns, the 3HP and water exit in the distillate, while impurities such as oligomers of 3HP and residual sugars exit from the bottoms of the columns. The first column operates at a pressure of 35 mmHg and an internal temperature of 135° C. The feed to the second distillation column is the unvaporized bottom product from the first distillation step. The second column operates at a pressure of 3 mmHg and a temperature of from 125° C. The distillates from the distillation columns are condensed in a condenser against chilled water, resulting in a final product of 60% 3HP by weight.

This example (when compared with example 12 below) provides lower capital and energy costs when compared to the example 12.

Example 12

Figure 3:
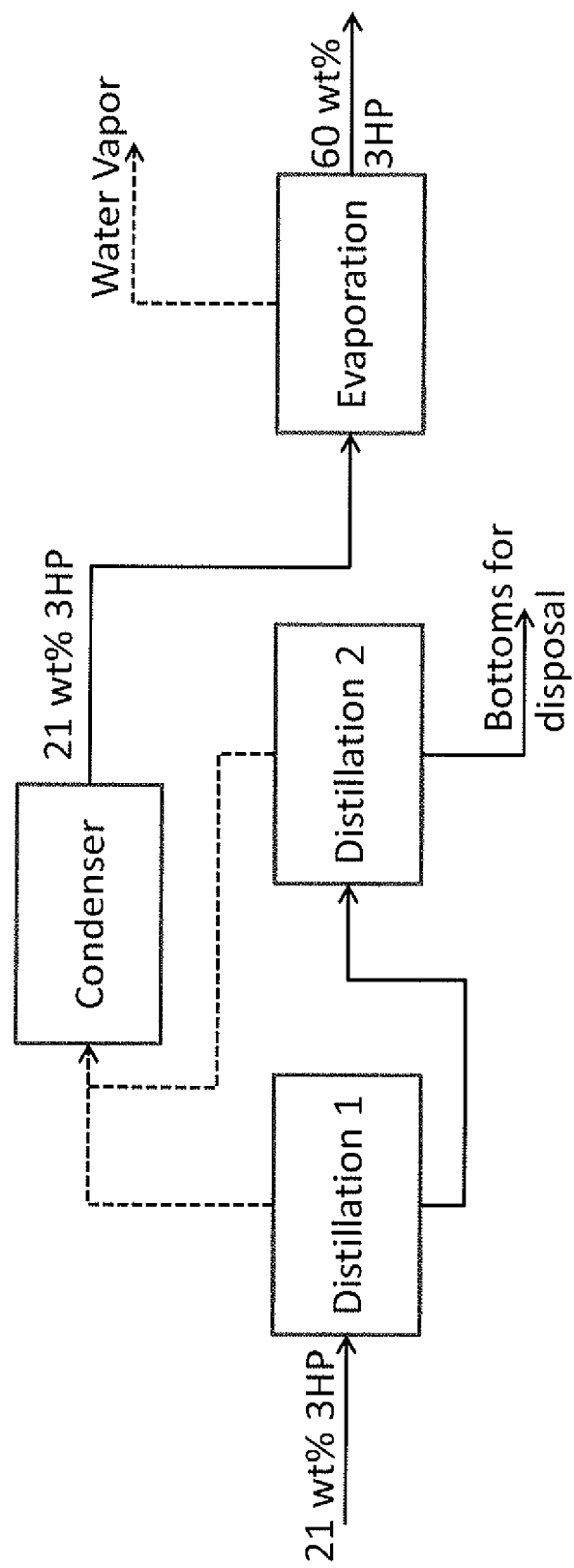
FIG. 3 is a process flow diagram depicting the processing steps described in Example 12.

Referring to FIG. 3, if higher overall recovery of 3HP from the fermentation broth is desirable at the expense of higher energy costs and higher capital costs, then example 12 is preferable. Example 12 contains the same unit operations as Example 11, but order in which the operations are carried out has been modified.

In this example, the 3HP containing reduced ion aqueous solution from Example 10 is fed to a series of two distillation columns. In these columns, the 3HP and water exit in the distillate, while impurities such as oligomers of 3HP and residual sugars exit from the bottoms of the columns. The first column operates at a pressure of 35 mmHg and an internal temperature of 135° C. The second column operates at a pressure of 3 mmHg and a temperature of 125° C. to 150° C. The distillates from the distillation columns are condensed in a condenser against chilled water, resulting in a final product of 21% 3HP by weight. When compared to Example 11, the concentration of 3HP is lower in the distillation column in Example 12. This allows the column to operate at lower temperatures and impacts the thermodynamics to increase the overall recovery of 3HP. The lower concentration also means that additional water must be vaporized into the distillate (leading to increased energy costs) and a larger total unit is required to vaporize a larger volume.

The distilled broth is then fed to a three stage thermal vapor recompression system. There, under the conditions of 0.39 bar pressure and each stage has a temperature of 80° C. to 85° C., the concentration of the demineralized broth is increased from 21 wt % 3HP to 60 wt % 3HP. Condensed water vapor from the evaporation process is recycled for use in fermentation and/or for flushing the demineralization.

Example 13

The distillation step of either Example 11 or Example 12 may be modified by adding an optional steam stripping. In steam stripping, steam is added to the bottom of the distillation column, providing additional mass into which 3HP can vaporize. This has the effect of increasing the overall recovery of 3HP from the process, while increasing energy usage, and reducing the final concentration of the recovered 3HP. Steam stripping would typically be utilized with a 3HP containing reduced ion aqueous solutions having at least 40 wt % 3HP, preferably at least 50 wt % 3HP.

Figure 4:
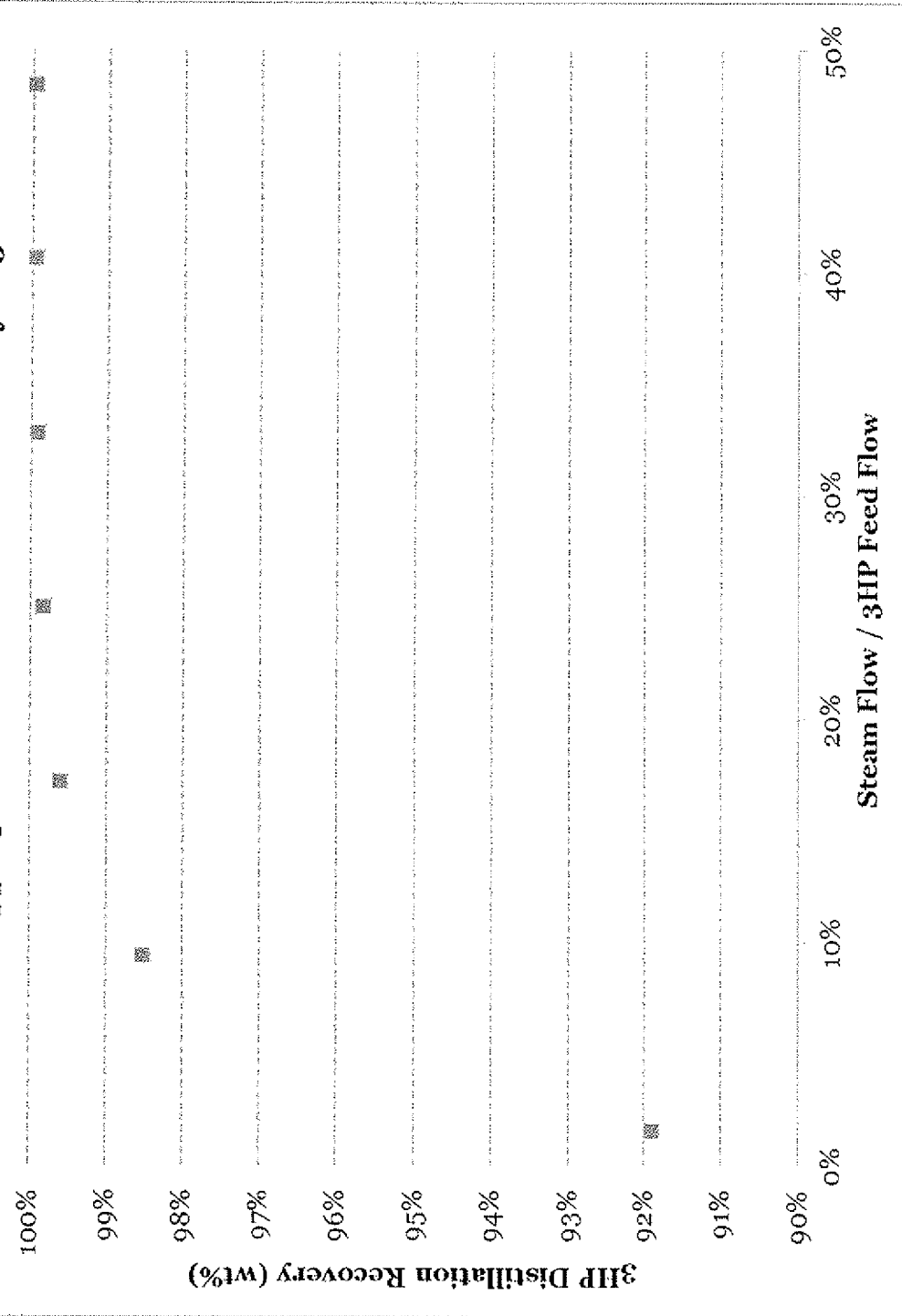
FIG. 4 is graph showing the effect of adding steam to a distillation system that is being fed a reduced ion aqueous solution containing 60 percent by weight 3HP.

As an example, but in no way limiting its use, FIG. 4 demonstrates the effect of adding stripping steam to total recovery on a distillation column with a 60 wt % 3HP feed. FIG. 4 shows that as the feed rate of steam introduced into a distillation system is increased (relative to the feed rate of 3HP containing solution), the percent of overall 3HP that is recovered in the distillate increases. However, in general as ratio of steam feed rate: 3HP feed rate increases, the energy usage required increases and the concentration of 3HP in the distillate decreases.

The energy costs and yields obtained from Examples 11 and 12, with and without steam stripping, are listed in Table 13-1 below:

TABLE 13-1

Comparison of 3HP recovery and energy usage based on the configuration of the evaporation and distillation steps.

| Example | Change in 3HP Recovery (% Relative Example 11) | Energy Usage in evaporation and distillation (Relative to Example 11) | Final 3HP concentration (wt %) |
|---|---|---|---|
| Example 11 | 0% | 1.0 | 60 wt % |
| Example 12 | 3% | 1.75 | 60 wt % |
| Example 11 with Steam Stripping | 3% | 1.2 | 55 wt % |

Table 13-1 shows that the relative recovery of 3HP from a method that uses evaporation before distillation is slightly lower than the recovery from a method first distills the 3HP and then increases the concentration using evaporation. However, as can be seen from Table 13-1, a system that uses a distillation step to separate 3HP from other components of a 3HP containing reduced ion aqueous solution and then utilizes evaporation to increase the concentration of the 3HP, utilizes far more energy than a comparable system as described in Example 11.

All patents, patent applications (including provisional applications), and publications cited herein are incorporated by reference as if individually incorporated for all purposes. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for recovering a composition enriched in 3-hydroxypropionic acid from a fermentation broth comprising 3-hydroxypropionic acid and/or salts thereof, the method comprising the steps of:
    (a) providing the fermentation broth comprising from about 60 to about 150 grams of 3-hydroxypropionic acid equivalents per liter of broth and having a pH of from about 2 to about 5 comprising:
        3-hydroxypropionic acid and/or salts thereof, calcium ions, and
        a total sulfate ion and phosphate ion concentration;
    (b) acidifying the fermentation broth to lower the pH to from about 1 to about 3 to produce an isolatable compound comprising calcium and to form an aqueous solution comprising 3-hydroxypropionic acid;
    (c) reducing the total sulfate ion and phosphate ion concentration of the aqueous solution to produce a reduced ion aqueous solution comprising 3-hydroxypropionic acid;
    (d) distilling the reduced ion aqueous solution at a pH of from about 1 to about 3 by applying vacuum and heat to the reduced ion aqueous solution to form an aqueous distillation product comprising 3-hydroxypropionic acid;
    (e) recovering the aqueous distillation product comprising 3-hydroxypropionic acid at a concentration of at least twenty percent by weight of the aqueous distillation product and wherein the aqueous distillation product comprises less than five parts by weight acrylic acid per one hundred parts by weight 3-hydroxypropionic acid present;
    (f) recovering a distillation bottom stream from distilling step (d), the distillation bottom stream comprising from about 5 percent to about 20 percent 3-hydroxypropionic acid of the total amount of the 3-hydroxypropionic acid present in the reduced ion aqueous solution of step (c);
    (g) applying vacuum and heat to the distillation bottom stream; and
    (h) recovering a second aqueous distillation product comprising 3-hydroxypropionic acid, wherein the second aqueous distillation product comprises less than about three parts by weight acrylic acid per one hundred parts by weight 3-hydroxypropionic acid present in the second aqueous distillation product.

2. The method of claim 1, wherein the step (d) of distilling the reduced ion aqueous solution is carried out by equipment selected from wiped film evaporation equipment, rising film evaporator equipment, thin film evaporation equipment, centrifugal molecular distillation equipment, and falling film distillation equipment.

3. The method of claim 1, wherein water is added to the distillation bottom stream prior to step (g).

4. The method of claim 1, wherein the isolatable compound comprising calcium is removed during or after step (b).

5. The method of claim 4, wherein the isolatable compound comprises gypsum.

* * * * *